US010779857B2

(12) United States Patent
Kiev

(10) Patent No.: US 10,779,857 B2
(45) Date of Patent: Sep. 22, 2020

(54) DEVICE AND METHOD FOR ACCESS TO INTERIOR BODY REGIONS

(71) Applicant: AOK Innovations, LLC, Lexington, KY (US)

(72) Inventor: Jon Kiev, Lexington, KY (US)

(73) Assignee: AOK Innovations, LLC, Lexington, KY (US)

( * ) Notice: Subject to any disclaimer, the term of this patent is extended or adjusted under 35 U.S.C. 154(b) by 110 days.

(21) Appl. No.: 15/944,792

(22) Filed: Apr. 4, 2018

(65) Prior Publication Data
US 2019/0307485 A1 Oct. 10, 2019

(51) Int. Cl.
A61B 17/34 (2006.01)
A61B 17/3209 (2006.01)
A61B 17/00 (2006.01)
A61B 90/00 (2016.01)

(52) U.S. Cl.
CPC .... *A61B 17/3423* (2013.01); *A61B 17/32093* (2013.01); *A61B 17/3415* (2013.01); *A61B 17/3496* (2013.01); *A61B 2017/00367* (2013.01); *A61B 2017/00477* (2013.01); *A61B 2017/347* (2013.01);
(Continued)

(58) Field of Classification Search
CPC .......... A61B 17/3423; A61B 17/3496; A61B 17/3415; A61B 17/32093; A61B 17/34; A61B 2017/00367; A61B 2017/345; A61B 2017/00477; A61B 2017/347; A61B 2017/0046; A61B 2017/346; A61B 2017/3454; A61B 2090/0808; A61B 2090/0811; A61B 2217/005; A61M 29/00; A61M 25/00

USPC .............................. 606/185; 604/164.01–12
See application file for complete search history.

(56) References Cited

U.S. PATENT DOCUMENTS 4,535,773 A 8/1985 Yoon
5,066,288 A 11/1991 Deniega et al.
5,152,754 A 10/1992 Plyley et al.
(Continued)

FOREIGN PATENT DOCUMENTS

CN 2252603 Y 4/1997
EP 0135364 A2 3/1985
WO WO2014006403 1/2014

OTHER PUBLICATIONS

U.S. Appl. No. 16/782,689, Device and Method for Access to Interior Body Regions, filed Feb. 5, 2020.

*Primary Examiner* — Katherine M Shi
*Assistant Examiner* — Alyssa M Keane
(74) *Attorney, Agent, or Firm* — Marshall, Gerstein & Borun LLP

(57) ABSTRACT

A device and method is provided to gain access to interior body regions. The system includes a safety needle, a stylet assembly, a blade assembly, an obturator assembly, a cannula assembly, a handle assembly, an actuator assembly, and a lock assembly. The safety needle accesses an interior body region. The actuator assembly, lock assembly, and handle assembly interact to expose the blade assembly, after which the blade assembly expands the pathway created by the safety needle. The obturator then further expands the pathway and delivers the cannula assembly to the desired location. The safety needle, obturator assembly, blade assembly, handle assembly, actuator assembly, and lock assembly are removed, leaving the cannula assembly in place for future procedures.

9 Claims, 12 Drawing Sheets

(52) U.S. Cl.
CPC .............. *A61B 2017/3456* (2013.01); *A61B 2090/0808* (2016.02); *A61B 2217/005* (2013.01)

(56) References Cited

U.S. PATENT DOCUMENTS

| | | | |
|---|---|---|---|
| 5,295,977 A | 3/1994 | Cohen et al. | |
| 5,314,417 A | 5/1994 | Stephens et al. | |
| 5,342,382 A | 8/1994 | Brinkerhoff et al. | |
| 5,387,197 A | 2/1995 | Smith et al. | |
| 5,522,833 A | 6/1996 | Stephens et al. | |
| 5,624,459 A | 4/1997 | Kortenbach et al. | |
| 5,674,237 A | 10/1997 | Ott | |
| 5,779,680 A | 7/1998 | Yoon | |
| 5,843,115 A | 12/1998 | Morejon | |
| 5,855,566 A | 1/1999 | Dunlap et al. | |
| 5,984,941 A | 11/1999 | Wilson et al. | |
| 6,017,356 A * | 1/2000 | Frederick .......... | A61B 17/3417 604/264 |
| 6,056,766 A | 5/2000 | Thompson | |
| 6,063,099 A | 5/2000 | Danks et al. | |
| 6,156,006 A | 12/2000 | Brosens et al. | |
| 6,402,770 B1 | 6/2002 | Jessen | |
| 6,447,527 B1 | 9/2002 | Thompson et al. | |
| 6,613,063 B1 | 9/2003 | Hunsberger | |
| 7,344,519 B2 | 3/2008 | Wing et al. | |
| 7,367,960 B2 | 5/2008 | Stellon et al. | |
| 7,419,496 B2 | 9/2008 | Staudner | |
| 7,731,730 B2 | 6/2010 | Popov | |
| 8,419,764 B2 | 4/2013 | Begg | |
| 8,801,741 B2 | 8/2014 | Ahlberg et al. | |
| 8,940,007 B2 | 1/2015 | Smith et al. | |
| 9,743,952 B2 | 8/2017 | Kiev | |
| 9,743,953 B2 | 8/2017 | Kiev | |
| 10,588,658 B2 | 3/2020 | Kiev | |
| 2007/0270819 A1 | 11/2007 | Justis et al. | |
| 2008/0009894 A1 | 1/2008 | Smith | |
| 2012/0116418 A1 | 5/2012 | Belson | |

\* cited by examiner

DEVICE AND METHOD FOR ACCESS TO INTERIOR BODY REGIONS

TECHNICAL FIELD

The present invention relates to devices and methods to access interior body regions. More particularly, it relates to devices and methods used to create space to insert a tube into a patient.

BACKGROUND

Embodiments of the invention relate to devices to create access to interior body regions and methods of using the devices.

There are many instances in which a practitioner must access the chest, abdomen, or pelvis, and insert a drainage tube, or chest tube. Examples of these instances include: collapsed lung, lung infection, bleeding in the chest cavity, fluid or air buildup due to other medical conditions or trauma, and prior surgery.

The traditional way of inserting a chest tube begins with the practitioner prepping the side of the body for the chest tube by sterilizing the area. Using a scalpel, the practitioner then makes a small incision (skin nick), between the ribs closest to the desired location in the chest. Then, using a combination of blunt dissection and surgical clamps, the practitioner will slowly open the space and extend it into the chest cavity. Once the practitioner confirms she has reached the desired space, the chest tube is inserted and sutured in place to prevent slippage.

Critics claim that the traditional method of chest tube insertion is barbaric and does not take advantage of advances in technology that can make the insertion process safer and more effective. Some companies have designed devices, called trocars, to facilitate safer and easier chest tube placement without using multiple, separate components.

Many groups of trocars include a combination of an access needle, an obturator and a dilator. The doctor advances the device against the skin and interior body regions using the access needle. As the doctor advances the device through the body, the obturator expands the pathway created by the access needle. When the device reaches the desired area, the practitioner removes the safety needle and the obturator from the dilator, leaving the dilator in place. The practitioner then pushes the chest tube through the dilator and removes the dilator, leaving the chest tube in the desired location.

Problems arise with these types of trocars, however, because the obturator does not actually work very well in expanding the pathway created by the relatively small access needle. The skin provides a tough membrane that resists expansion, and additional skin nicks (using a separate scalpel) are required around the access needle to allow the obturator to properly expand the skin layer and continue to penetrate deeper into the body.

To address this issue, other groups of trocars employ a retractable blade instead of an access needle. The blade is used to create a larger skin nick and advance through other tissues as needed until reaching the desired location. The obturator easily expands the pathway as it passes through the skin layer while the practitioner advances the device, and then the blade is retracted and the blade/obturator combination is removed, leaving the dilator in place for the chest tube.

While these groups of trocars address the issue of requiring an additional scalpel to allow the obturator to expand the skin layer, they do not include the access needle that prevents the doctor from progressing too quickly or too far and causing harm to the patient. Without the access needle as part of the system, the patient is at a greater risk of complications.

What is needed in the market is an all-in-one trocar device that provides the ability to create a skin nick and maintain safety as the device is inserted deeper into the body, while quickly accessing the desired location for chest tube placement.

BRIEF SUMMARY OF THE INVENTION

Benefits achieved in accordance with principles of the disclosed invention include a device that provides access to interior body regions.

Some aspects of the present invention relate to a safety needle, a blade assembly, an obturator assembly, a cannula assembly, and a handle assembly. The safety needle, blade assembly, obturator assembly, cannula assembly, and handle assembly are assembled to create an access device.

In some aspects of the present invention, the handle assembly further includes an actuator assembly and a lock assembly.

In other aspects of the present invention, the safety needle includes a hub through which fluid may be drawn in order to confirm the access device has reached the proper location within the body.

In further aspects of the present invention, the blade assembly and obturator assembly are fixed relative to the handle assembly and the actuator assembly and lock assembly are moveable relative to the handle assembly.

In additional aspects of the present invention, moving the actuator assembly relative to the handle assembly may expose blades through blade slots located on the blade assembly.

In yet other aspects of the present invention, the lock assembly may be positioned to permit or prevent movement of the actuator assembly relative to the handle assembly.

Yet other aspects of the present invention relate to a method of accessing interior body regions in which the safety needle assembly is advanced through skin and into interior body regions to create a pathway. The blades of the blade assembly are exposed and the blade assembly is advanced into the skin to create a skin nick, after which the blades are covered. The access device is then advanced into the tissue, and the obturator assembly increases the diameter of the pathway created by the safety needle. After the access device is in the proper location, the safety needle assembly, blade assembly, and obturator assembly are removed from the cannula assembly, leaving the cannula assembly in the body to provide a conduit through which other devices may be inserted.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Figure 1:
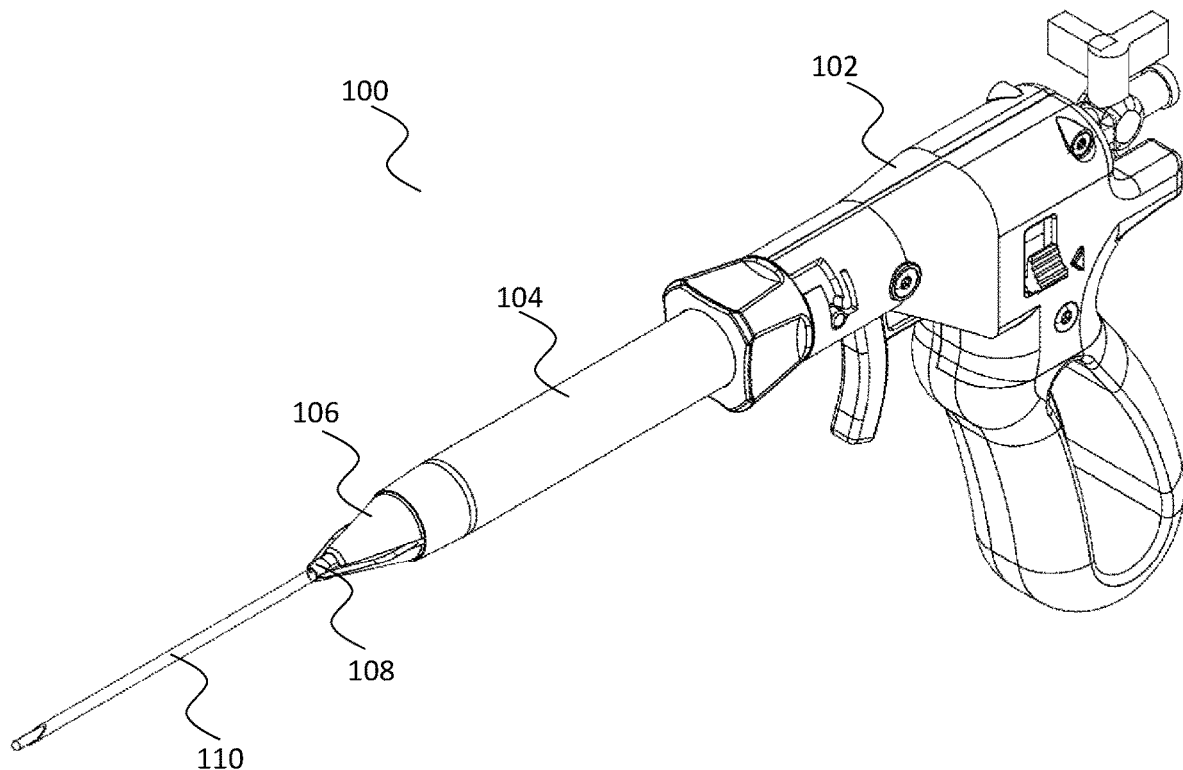
FIG. 1 illustrates an access device according to aspects of the present invention.

FIG. 1 illustrates an access device according to aspects of the present invention.

As shown in the figure, access device 100 includes handle assembly 102, cannula assembly 104, obturator assembly 106, blade assembly 108, and safety needle 110.

Specific aspects of handle assembly 102, cannula assembly 104, obturator assembly 106, blade assembly 108, and safety needle 110 will be further described with reference to FIGS. 2-4.

In general, safety needle 110 creates a pathway through the skin of a patient and into a target region. Then, blade assembly 108 creates a skin nick to expand the size of the pathway to allow obturator assembly 106 to increase the diameter of the pathway. Obturator assembly 106 increases the diameter of the pathway when the user pushes handle assembly 102 toward the patient, urging obturator assembly 106 into the pathway. When obturator assembly 106 is in the target region, cannula assembly 104 is disconnected from handle assembly 102, and cannula assembly 104 is left within the patient for further procedural steps.

A detailed description of the assembly and operation of access device will now be described with reference to FIGS. 2-13.

Figure 2:
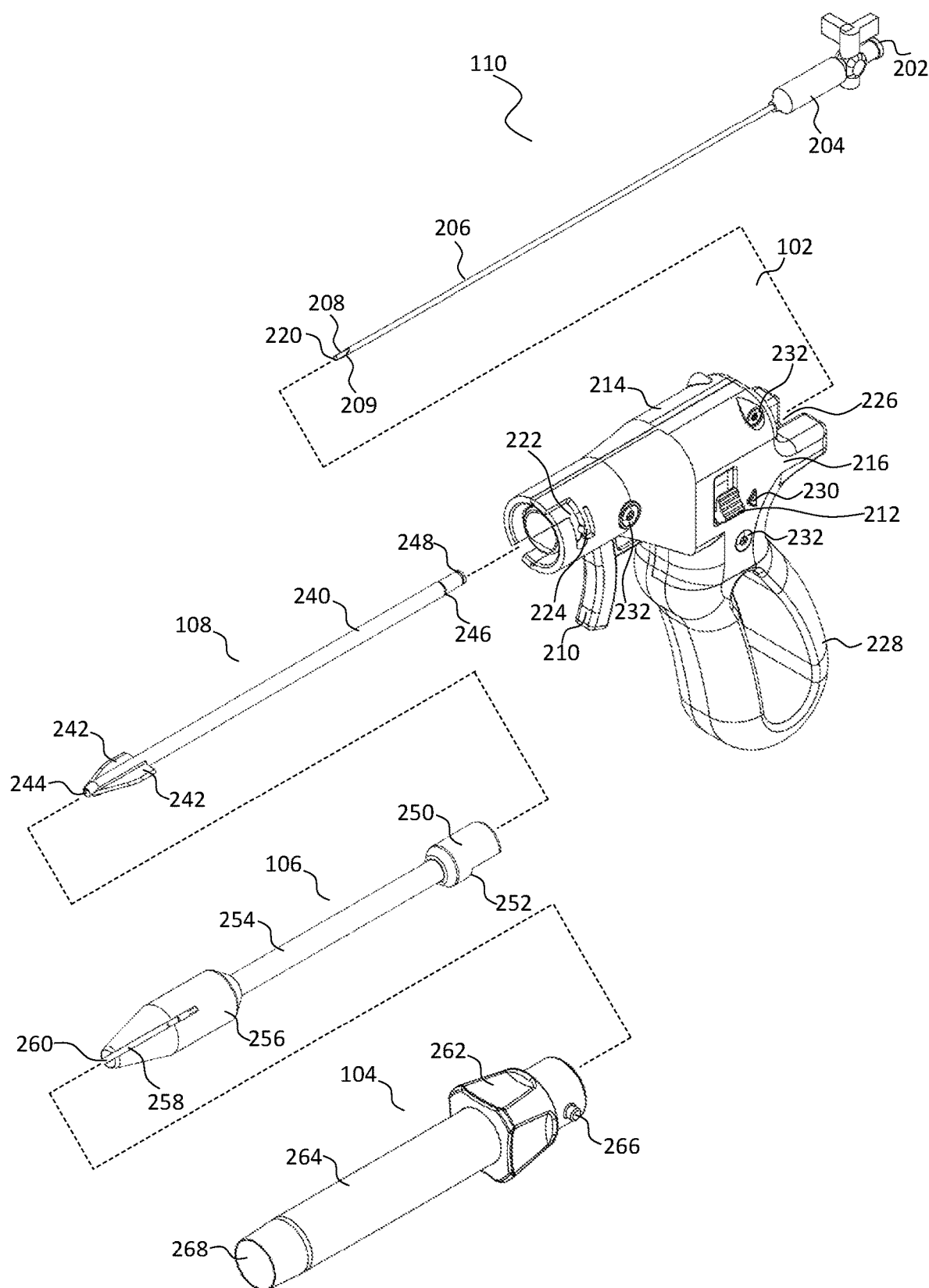
FIG. 2 illustrates an exploded view of an access device according to aspects of the present invention.

FIG. 2 illustrates an exploded view of an access device according to aspects of the present invention.

As shown in the figure, safety needle 110 further includes a connection 202, a hub 204, an outer cannula 206, an inner cannula 208, a sharp tip 209, and a blunt tip 220.

Safety needle 110 is similar to the safety needle described in U.S. Pat. No. 9,743,952, and the description of the safety needle is incorporated herein by reference. Therefore, safety needle 110 will not be described here in detail, but an overview of the operation of safety needle 110 will be described below.

Safety needle 110 is also referred to as a "veress needle" by physicians and other clinicians. Outer cannula 206 and inner cannula 208 are typically made from a surgical grade stainless steel, however any material suitable for patient contact may be used. Hub 204 and connector 202 are typically made from a molded plastic, however any material suitable for connection to outer cannula 206 and inner cannula 208 may be used.

Safety needle 110 is designed to prevent unnecessary needle sticks to the patient because blunt tip 220 extends beyond sharp tip 209, therefore the first portion of safety needle 110 to contact a patient is blunt tip 220. When blunt tip 220 contacts the patient and safety needle 110 continues to be pushed toward the patient, sharp tip 209 extends forward until sharp tip 209 contacts the patient and begins to cut tissue. When sharp tip 209 has cut through tissue and reaches a pocked of air or fluid, blunt tip 220 is urged forward by a spring located in hub 204 until blunt tip 220 is distal to sharp tip 209, and again sharp tip 209 is prevented from causing unwanted needle sticks to the patient.

Blade assembly 108 further includes a blade shaft 240, blades 242, a lumen 244, a groove 246, and a groove 248.

Blade shaft 240 is a rigid tube and is preferably made of metal, however any other rigid material would suffice. Blade shaft 240 is connected to blades 242 such that there is no relative motion between the two components. The connection is preferably a welded connection, however other connection means may be employed. For example, blade shaft 240 may include one or more slots at its distal end and blades 242 may include one or more matching slots such that blades 242 may be assembled on to blade shaft 240 by sliding slotted sections of blades 242 on to the corresponding slots at the distal end of blade shaft 240.

Blades 242 are preferably constructed from metal, more preferably from stainless steel, however any material suitable for medical applications would suffice. Blades 242 are designed to cut the skin and other tissues of a patient, and as such are sufficiently sharp to cut skin and tissue. The specific shape, grind angles, and tip angles may be of any dimensions such that the effect of cutting skin and tissue may be accomplished. Blades 242 are attached to blade shaft 240 as previously described.

Grooves 246 and 248 are located near the proximal end of blade shaft 240. Grooves 246 and 248 are circumferential recesses cut into the outer wall of blade shaft 240, but grooves 246 and 248 do not breach the inner wall of blade shaft 240.

Lumen 244 is an opening that extends through the entire longitudinal length of blade shaft 240, providing a space through which safety needle 110 can be inserted and removed.

Obturator assembly 106 further includes a proximal end 250, an obturator shaft 254, a distal end 256, and a lumen 260. All components of obturator assembly 106 are preferably made from plastic via either machining or molding processes, however any suitable material or manufacturing method may be used to create obturator assembly 106 and its components.

Distal end 256 enlarges openings in skin and tissue, and further includes blade slot 258. Blade slot 258 provides a pathway for blades 242 to be deployed beyond the distal-most portion of distal end 256 and to be fully retracted within distal end 256. Distal end 256 is connected obturator shaft 254 by any suitable means that would prevent relative motion between the two components. In an alternate embodiment, distal end 256 and obturator shaft 254 may be a single component.

Obturator shaft 254 travels within the enlarged opening created by distal end 256. As shown in the figure, obturator shaft 254 is a tube with no slots or cuts in its outer diameter. In an alternate embodiment, obturator shaft 254 may contain slots or cuts that extend from the outer diameter of obturator shaft 254 through the inner diameter of obturator shaft 254. Including the slots or cuts may reduce weight and/or manufacturing complexity or cost.

Proximal end 250 is connected to obturator shaft 254 by any means that would create a bond to prevent relative motion between the two components. Proximal end 250 further includes shelf 252 such that shelf 252 causes the cross section of proximal end 250 to be asymmetric. Shelf 252 prevents relative motion between proximal end 250 and handle assembly 102 and permits proximal end 250 to be inserted into handle assembly 102 in only one orientation.

Lumen 260 is an opening that extends through the entire longitudinal length of obturator assembly 106, providing a space through which blade assembly 108 can be inserted and removed.

Cannula assembly 104 further includes a cannula hub 262, a cannula shaft 264, a protrusion 266, and a lumen 268. All components of cannula assembly 104 are preferably made from plastic via either machining or molding processes, however any suitable material or manufacturing method may be used to create cannula assembly 104 and its components.

Cannula hub 262 is connected to cannula shaft 264 by any means that would create a bond to prevent relative motion between the two components. Cannula hub 262 further includes a protrusion 266 that is sized and configured to fit within a slot on handle assembly 102. As shown in the figure, one protrusion 266 is included on cannula hub 262, however in an alternate embodiment more than one protrusion may be included.

Lumen 268 is an opening that extends through the entire longitudinal length of cannula assembly 104, providing a space through which obturator assembly 106 can be inserted and removed.

Handle assembly 102 further includes an actuator assembly 210, a lock assembly 212, a handle half 214, a handle half 216, a cannula slot 222, a cannula slot tab 224, a safety slot 226, a user grip 228, an indicator 230, and assembly holes 232. Actuator assembly 210 and lock assembly 212 will be further described with reference to FIG. 3.

Handle half 214 and 216 are preferably made from plastic via either machining or molding processes, however any suitable material or manufacturing method may be used. Handle half 214 and handle half 216 each include at least one assembly hole 232 such that when handle half 214 and handle half 216 are assembled together, corresponding assembly holes 232 line up with each other. Assembly holes 232 may be threaded such that a threaded connector could be used to connect corresponding assembly holes 232. In an alternate embodiment, assembly holes 232 may be unthreaded such that an unthreaded connector may be used to connect corresponding assembly holes 232. In yet another alternate embodiment, assembly holes 232 could be replaced with snap fit connections.

Cannula slot 222 is a groove that extends from the outer wall of handle half 216 through the inner wall of handle half 216. Cannula slot 222 begins at the distal end of handle half 216 and extends parallel to the longitudinal axis of handle assembly 102. Then cannula slot 222 extends circumferentially around handle half 216. As shown in the figure, cannula slot 222 is shaped like an "L", however in alternate embodiments cannula slot 222 may be shaped differently. Cannula slot 222 is sized and configured to receive protrusion 266. As shown in the figure, cannula slot 222 is locate on handle half 216, however there may be another cannula slot 222 located on handle half 214.

Cannula slot tab 224 is a tab disposed on the circumferential portion of cannula slot 222. Cannula slot tab 224 may include a living hinge to allow cannula slot tab to flex when subjected to a force. Cannula slot tab 224 is sized and configured to contact protrusion 266.

Safety slot 226 is located on the proximal end of handle assembly 102. Safety slot 226 is sized and configured to receive hub 204 of safety needle 110.

User grip 228 is the portion of handle assembly 102 that will be held by the user. The size, shape, and configuration of user grip 228 as shown in the figure is a preferred embodiment, however any alternate sizes, shapes, or configurations of user grip 228 that allow a user to grip handle assembly 102 may be implemented.

Indicator 230 is disposed on handle half 216 and is a visual indicator of the position of lock assembly 212. Indicator 230 may be triangular as shown in the figure, but any other shape sufficient to provide indication to a user may be used. In some embodiments, indicator 230 may be molded in to the plastic of handle half 216, however in other embodiments indicator 230 may be added to handle half 216 after the molding process. In those other embodiments, indicator 230 may be a sticker affixed to handle half 216 or a more permanent marking like ink, paint, or dye. As shown in the figure, indicator 230 is located on handle half 216, however in other embodiments indicator 230 may be located on one or both of handle half 214 and 216.

To assemble access device 100, blade assembly 108 is assembled to obturator assembly 106. This assembly can be accomplished by inserting the proximal end of blade assembly 108 into the distal end of lumen 260. The combination of blade assembly 108 and obturator assembly 106 is then assembled into handle assembly 102. Safety needle 110 is then inserted through lumen 244 and hub 204 rests in safety slot 226. Cannula assembly 104 is then attached to handle assembly 102 by inserting protrusion 266 into cannula slot 222 first in the longitudinal direction, and then by rotating cannula assembly 104 such that protrusion 266 follows cannula slot 222. When protrusion 266 contacts cannula slot tab 224, cannula slot tab deflects to allow protrusion 266 to be rotated beyond cannula slot tab 224. When protrusion 266 is past cannula slot tab 224, cannula slot tab 224 returns to its original position. Additional assembly details will be further described with reference to FIGS. 3-4.

Figure 3:
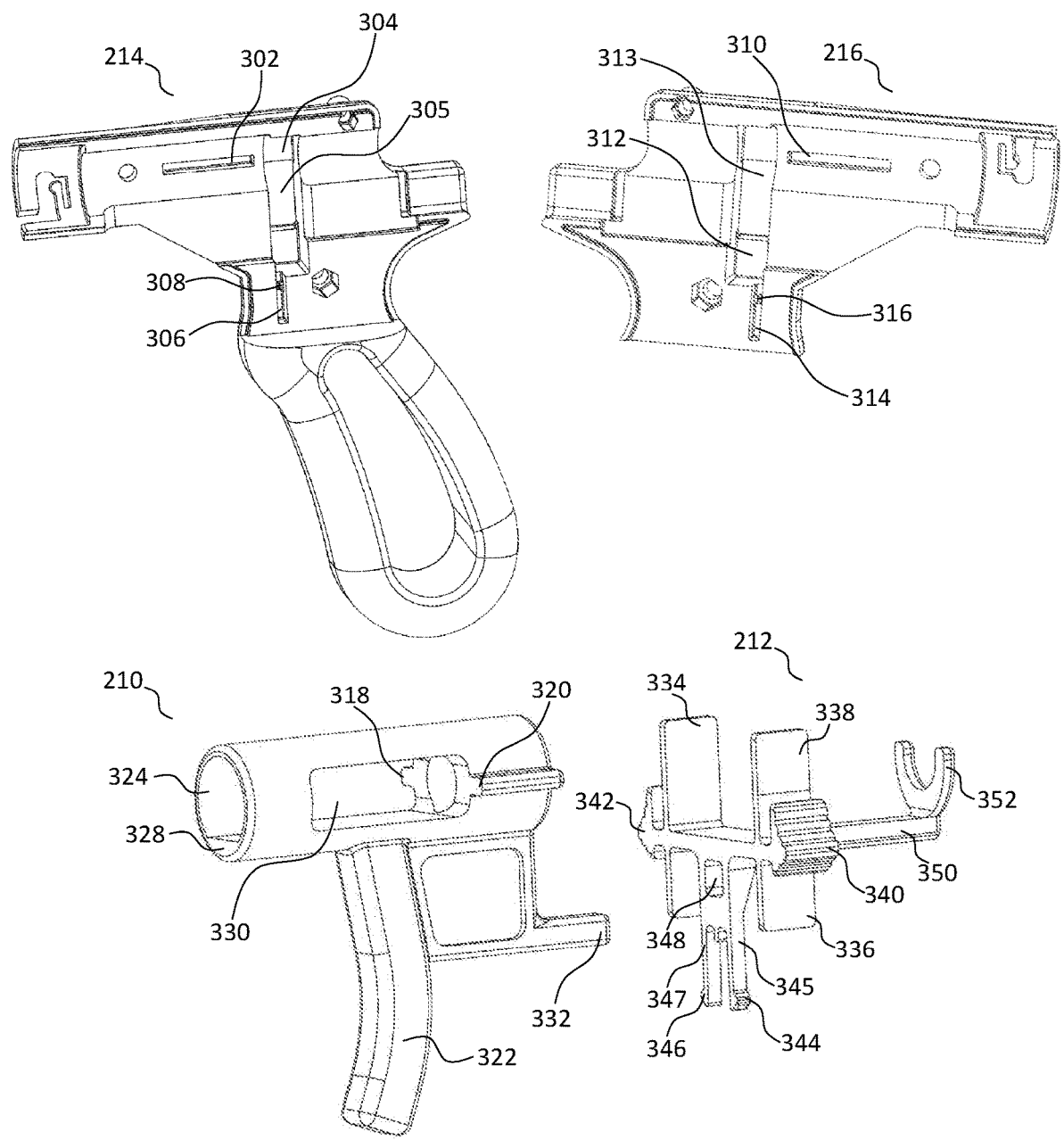
FIG. 3 illustrates an exploded view of a handle assembly according to aspects of the present invention.

FIG. 3 illustrates an exploded view of a handle assembly according to aspects of the present invention.

As shown in the figure, handle half 214 further includes a longitudinal slot 302, a transverse slot 304, a window 305, a locking slot 306, and a projection 308. Handle half 216 further includes a longitudinal slot 310, a transverse slot 312, a window 313, a locking slot 314, and a projection 316. Actuator assembly 210 includes an actuator tab 318, an actuator tab 320, a trigger 322, a lumen 324, a flat section 328, an assembly window 330, and an actuator stem 332. Lock assembly 212 includes a locking rail 334, a locking rail 336, a visual indicator 338, a button 340, a button 342, a locking tab 344, a locking stem 345, a locking tab 346, a locking stem 347, a locking aperture 348, a stem 350, and a safety needle lock 352.

Actuator assembly 210 and lock assembly 212 are preferably made from plastic via either machining or molding processes, however any suitable material or manufacturing method may be used.

Longitudinal slot 302 is a recess within the inner wall of handle half 214, and longitudinal slot 302 is sized and configured to slidably receive actuator tab 318.

Transverse slot 304 is a recess within the inner wall of handle half 214, and transverse slot 304 is sized and configured to slidably receive locking rail 334.

Window 305 is a cut that extends through transverse slot 304 from the inner wall of handle half 214 through the outer wall of handle half 214, and window 305 is sized and configured to slidably receive button 342.

Locking slot 306 is a recess within the inner wall of handle half 214, and locking slot 306 is connected to, and extends from, transverse slot 304. Locking slot 306 is sized and configured to slidably receive locking stem 347.

Projection 308 is a protrusion within locking slot 306, and projection 308 is sized and configured to interact with locking tab 346.

Longitudinal slot 310 is a recess within the inner wall of handle half 216, and longitudinal slot 310 is sized and configured to slidably receive actuator tab 320.

Transverse slot 312 is a recess within the inner wall of handle half 216, and transverse slot 312 is sized and configured to slidably receive locking rail 336.

Window 313 is a cut that extends through transverse slot 312 from the inner wall of handle half 216 through the outer wall of handle half 216, and window 313 is sized and configured to slidably receive button 340.

Locking slot 314 is a recess within the inner wall of handle half 216, and locking slot 314 is connected to, and extends from, transverse slot 312. Locking slot 314 is sized and configured to slidably receive locking stem 345.

Projection 316 is a protrusion within locking slot 314, and projection 316 is sized and configured to interact with locking tab 344.

Actuator tab 318 and actuator tab 320 are projections that extend from the main body of actuator assembly 210. Actuator tab 318 is sized and configured to fit within longitudinal slot 302, and actuator tab 320 is sized and configured to fit within longitudinal slot 310. The length of actuator tabs 318 and 320 is shorter than the lengths of longitudinal slots 302 and 310. The difference in lengths allows actuator tab 318 to slide within longitudinal slot 302 and actuator tab 320 to slide within longitudinal slot 310.

Trigger 322 is a projection that extends from the main body of actuator assembly 210, and trigger 322 is sized and configured to allow at least one of the user's fingers to pull on trigger 322.

Lumen 324 is an opening that extends from the proximal end of actuator assembly 210 through the distal end of actuator assembly 210. Lumen 324 is sized and configured to provide space in which other components may be assembled and manipulated.

Flat section 328 is located near the distal end of lumen 324. Flat section 328 is an area that is not rounded to provide for easier assembly of components such that one or more components may only be assembled in one orientation.

Assembly window 330 is a cut that extends from the outer wall of actuator assembly 210 through the inner wall of actuator assembly 210, providing access to lumen 324 from an axis transverse to the longitudinal axis of actuator assembly 210. Assembly window 330 provides for easier manufacturing by allowing increased access to components during the assembly process.

Actuator stem 332 is a projection that extends along the longitudinal axis of actuator assembly 210. Actuator stem is sized and configured to fit within and through locking aperture 348 on lock assembly 212.

Locking rail 334 and locking rail 336 are projections that extend from the main body of lock assembly 212. Locking rail 334 is sized and configured to fit within transverse slot 304, and locking rail 336 is sized and configured to fit within transverse slot 312. The length of locking rails 334 and 336 is shorter than the lengths of transverse slots 304 and 312. The difference in lengths allows locking rail 334 to slide within transverse slot 304 and locking rail 336 to slide within transverse slot 312.

Visual indicator 338 is a portion of locking rail 336 that can be viewed through window 313 based on the position of lock assembly 212. Visual indicator 338 may be a different color than the rest of lock assembly 212 or actuator assembly 210 such that the user can see the color difference when visual indicator 338 is viewable through window 313. Another visual indicator may be included on locking rail 334 such that it would be viewable through window 305.

Button 340 and button 342 are projections that extend transversely from locking rails 336 and 334, respectively. Buttons 340 and 342 may be ribbed to provide a surface for a user to manipulate. Button 342 is sized and configured to extend through window 305, and button 340 is sized and configured to extend through window 313. Thus, when a user manipulates button 340 or 342, locking rails 334 and 336 may move up or down within transverse slots 304 and 312 depending on the direction of the force applied by the user, which causes lock assembly 212 to move up or down as well.

Locking stem 345 and locking stem 347 are projections that extend from the main body of lock assembly 212. Locking stem 345 is sized and configured to slidably fit within locking slot 314, and locking stem 347 is sized and configured to slidably fit within locking slot 306. The lengths of locking stems 345 and 347 is shorter than the length of locking slots 306 and 314. The difference in lengths allows locking stem 345 to slide within locking slot 314 and locking stem 347 to slide within locking slot 306.

Locking tab 344 and locking tab 346 are projections that extend from locking stem 345 and locking stem 347, respectively. Locking tab 344 is sized and configured to contact projection 316 and locking tab 346 is sized and configured to contact projection 308 such that a force is required to move locking tabs 344 and 346 past projections 316 and 308, respectively.

Locking aperture 348 is an opening located within lock assembly 212 that is aligned with the longitudinal axis of lock assembly 212. Locking aperture 348 is sized and configured to allow actuator stem 332 to pass through locking aperture 348 when locking aperture 348 and actuator stem 332 are coaxial with each other.

Stem 350 is a projection that extends proximally from the main body of lock assembly 212. Stem 350 provides a base for safety needle lock 352. Safety needle lock 352 is a semi cylindrical projection extending from stem 350. Safety needle lock 352 is sized and configured to interact with hub 204 of safety needle 110.

Figure 4A:
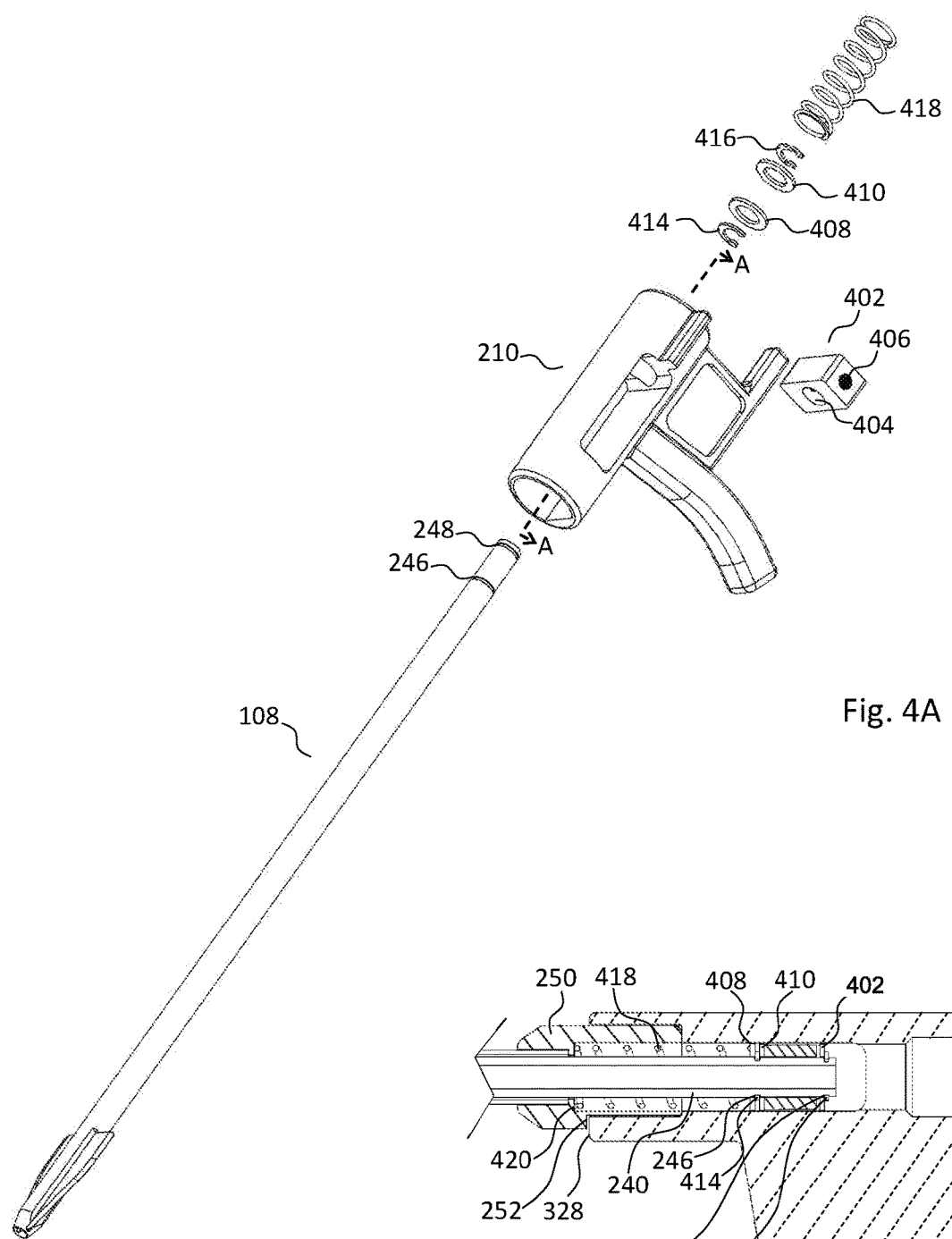
FIGS. 4A-B illustrate an exploded view of a blade assembly and actuator assembly according to aspects of the present invention.
Figure 4B:
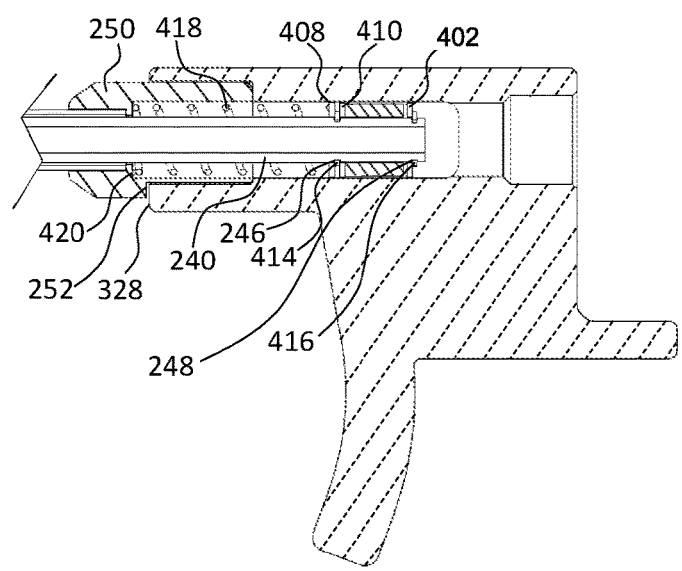

FIGS. 4A-B illustrate an exploded and assembled view of a blade assembly, actuator assembly, and obturator assembly according to aspects of the present invention.

As shown in the figures, additional components used for assembly include a spring rest 402, washers 408 and 410, retaining rings 414 and 416, and a spring 418.

Spring rest 402 further includes a hole 404 and a threaded hole 406. Spring rest 402 is preferably molded or machined from plastic, however any other suitable materials would suffice. Spring rest 402 acts as a stop for the proximal end of spring 418 such that when a compression force is applied to spring 418, spring rest 402 remains stationary and does not permit the proximal end of spring 418 to move. Spring rest 402 is also sized and configured to fit within assembly window 330. The longitudinal length of spring rest 402 is shorter than the longitudinal length of assembly window 330, thus allowing relative linear motion between spring rest 402 and actuator assembly 210.

Hole 404 is an opening that extends from the proximal end of spring rest 402 through the distal end of spring rest 402. Hole 404 is sized and configured to allow blade shaft 240 to pass through hole 404. The central axis of threaded hole 406 is perpendicular to the central axis of hole 404. FIG. 4A shows one hole 406, however there is a second hole 406 located 180 degrees opposite the threaded hole 406 shown in the figure. Threaded hole 406 is sized and configured to receive a threaded connector that is assembled through assembly holes 232. When a threaded connector is assembled to threaded hole 406 through assembly holes 232, spring rest 402 becomes fixed to handle assembly 102.

Retaining rings 414 and 416 are preferably metal components sized and configured to fit within grooves 246 and 248, respectively. The outer diameter of retaining rings 414 and 416 is larger than the outer diameter of blade shaft 240. Retaining rings 414 and 416 are not complete cylinders, and the free ends of retaining rings 414 and 416 flex slightly when assembling retaining rings 414 and 416 to grooves 246 and 248.

Washers 408 and 410 are preferably standard metal washers with an inner diameter sized and configured to fit around the outer diameter of blade shaft 240. The inner diameter of washers 408 and 410 is smaller than the outer diameter of retaining rings 414 and 416, thus when washers 408 and 410 contact retaining rings 414 and 416, washers 408 and 410 cannot move past retaining rings 414 and 416.

Spring 418 is preferably a standard helical spring with an inner diameter sized and configured to fit around the outer diameter of blade shaft 240 and retaining rings 414 and 416. The outer diameter of spring 418 is smaller than the outer diameter of washers 406 and 408.

FIG. 4B shows a cross-section taken along line A-A from FIG. 4A. As shown in FIG. 4B, proximal end 250 of obturator assembly 106 further includes a shelf 420. Shelf 420 is a cylindrical opening within proximal end 250 that is sized and configured to allow blade shaft 240 to extend through the opening. Shelf 420 is also sized and configured to contact spring 418.

To assemble actuator assembly 210, blade assembly 108, and obturator assembly 106, first blade assembly 108 is inserted into obturator assembly 106. To assemble, and with respect to FIG. 2 and FIG. 4, the proximal end of blade shaft 240 is inserted into lumen 260, and blade assembly 108 can be advanced through lumen 260 until blades 242 contact distal end 256 and prevent blade assembly 108 from advancing further. At this point, the proximal end of blade shaft 240 extends beyond proximal end 250. Retaining ring 414 is then assembled to groove 246. Spring 418 is then placed over retaining ring 414 and advanced toward proximal end 250 until the distal end of spring 418 contacts shelf 420.

Proximal end 250 is then inserted into lumen 324 of actuator assembly 210. Proximal end 250 can only be inserted in one orientation for proper assembly such that shelf 252 contacts flat section 328. Proximal end 250 may be adhered to actuator assembly 210 at this point in the process, however the connection may occur later in the assembly process.

Washer 408 is then placed over blade shaft 240 in one of two ways. First, washer 408 may be maneuvered through assembly window 330 and placed over blade shaft 240. Second, washer 408 may be dropped through the proximal end of lumen 324 and over blade shaft 240 such that wash 408 resets on retaining ring 414.

Spring rest 402 is then maneuvered through assembly window 330 and blade shaft 240 is placed through hole 404. In order to insert blade shaft 240 through hole 404 it may be necessary to compress spring 418. If compression of spring 418 is necessary, spring 418 must remain compressed while washer 410 is placed over blade shaft 240 and on top of spring rest 402, and while retaining ring 416 is connected to groove 248. After retaining ring 416 is connected to groove 248, spring rest 402 cannot move relative to blade assembly 108.

To complete the assembly of access device 100, and with reference to FIGS. 2-3, the assembled actuator assembly 210, blade assembly 108, and obturator assembly 106 is then placed on handle half 214 such that actuator tab 318 is within longitudinal slot 302. Then, locking rail 334 of lock assembly 212 is placed on handle half 214 such that locking rail 334 is within transverse slot 304. In addition, locking tab 346 may be placed on handle half 214 such that locking tab 346 is resting on top of projection 308.

In order to secure actuator assembly 210 in place, a threaded connector may be assembled through assembly hole 232 on handle half 214 that is longitudinally coaxial with threaded hole 406 of spring rest 402. The threaded connector would engage both handle half 214 and spring rest 402 such that actuator assembly 210 would not be dislodged from handle half 214 during the rest of the assembly process.

Subsequently, handle half 216 may be assembled to handle half 214 by aligning longitudinal slot 310 with actuator tab 320, transverse slot 312 with locking rail 336, and locking tab 344 with projection 316. After handle half 216 is properly placed, threaded connectors may be used to connect handle half 216 to handle half 214 by threading the threaded connectors through assembly holes 232 that are longitudinally coaxial with each other. An additional threaded connector may be used to engage handle half 216 and another threaded hole 406 of spring rest 402 such that spring rest 402 is connected to both handle half 214 and handle half 216.

After the threaded connections are complete, spring rest 402 and blade assembly 108 are in a fixed position relative to actuator assembly 210. Additionally, because the locking tab 346 is resting on top of projection 308 and locking tab 344 is resting on top of projection 316, locking aperture 348 is not coaxially aligned with actuator stem 332. As such, if a user attempted to pull trigger 322, actuator assembly 210 would not move relative to handle assembly 102 because actuator stem 332 would collide with lock assembly 212 just below locking aperture 348, preventing any movement.

Cannula assembly 104 may then be assembled to handle assembly 102 by inserting the combination of obturator assembly 106 and blade assembly 108 through lumen 268 until protrusion 266 contacts handle assembly 102. Cannula assembly 104 is then rotated until protrusion 266 is in line with cannula slot 222, and then cannula assembly 104 is advanced further toward handle assembly 102 with protrusion 266 within cannula slot 222. When protrusion 266 again contacts handle assembly 102, cannula assembly 108 is then rotated such that protrusion 266 continues to follow cannula slot 222. Protrusion 266 will then contact cannula slot tab 224. Cannula assembly 104 is rotated further such that protrusion 266 forces cannula slot tab 224 to elastically deform. When protrusion 266 passes cannula slot tab 224, cannula slot tab 224 returns to its original position, thus preventing cannula assembly 104 from being removed from handle assembly 102 unless a user reverses the steps required to assemble cannula assembly 108 to handle assembly 102.

Safety needle 110 is then assembled to access device 100 by inserting outer cannula 206 through lumen 244 until hub 204 contacts safety needle lock 352. To continue assembly, lock assembly 212 must be moved downward by pressing one or both of buttons 340 and 342 to urge lock assembly 212 downward. By doing so, locking tab 346 engages with projection 308 and locking tab 344 engages with projection 316. In order for locking tab 346 to move past projection 308, locking stem 347 must elastically deform. Likewise, in order for locking tab 344 to move past projection 316, locking stem 345 must elastically deform. After locking tabs 346 and 344 have passed projections 308 and 316, respectively, locking stems 345 and 347 return to their original configurations.

With lock assembly 212 in the downward, or unlocked, position, hub 204 of safety needle 110 may move past safety needle lock 352. When safety needle 110 can no longer move toward handle assembly 210, lock assembly 212 may be returned to the upward, or locked, position, by pushing one or both of buttons 340 and 342 upward until locking tabs 346 and 344 are above projections 308 and 316, respectively. With lock assembly in the locked position, safety needle lock 352 engages hub 204 such that hub 204 cannot move relative to handle assembly 210.

The operation of the components discussed above will now be described with reference to FIGS. 5-13.

Figure 5:
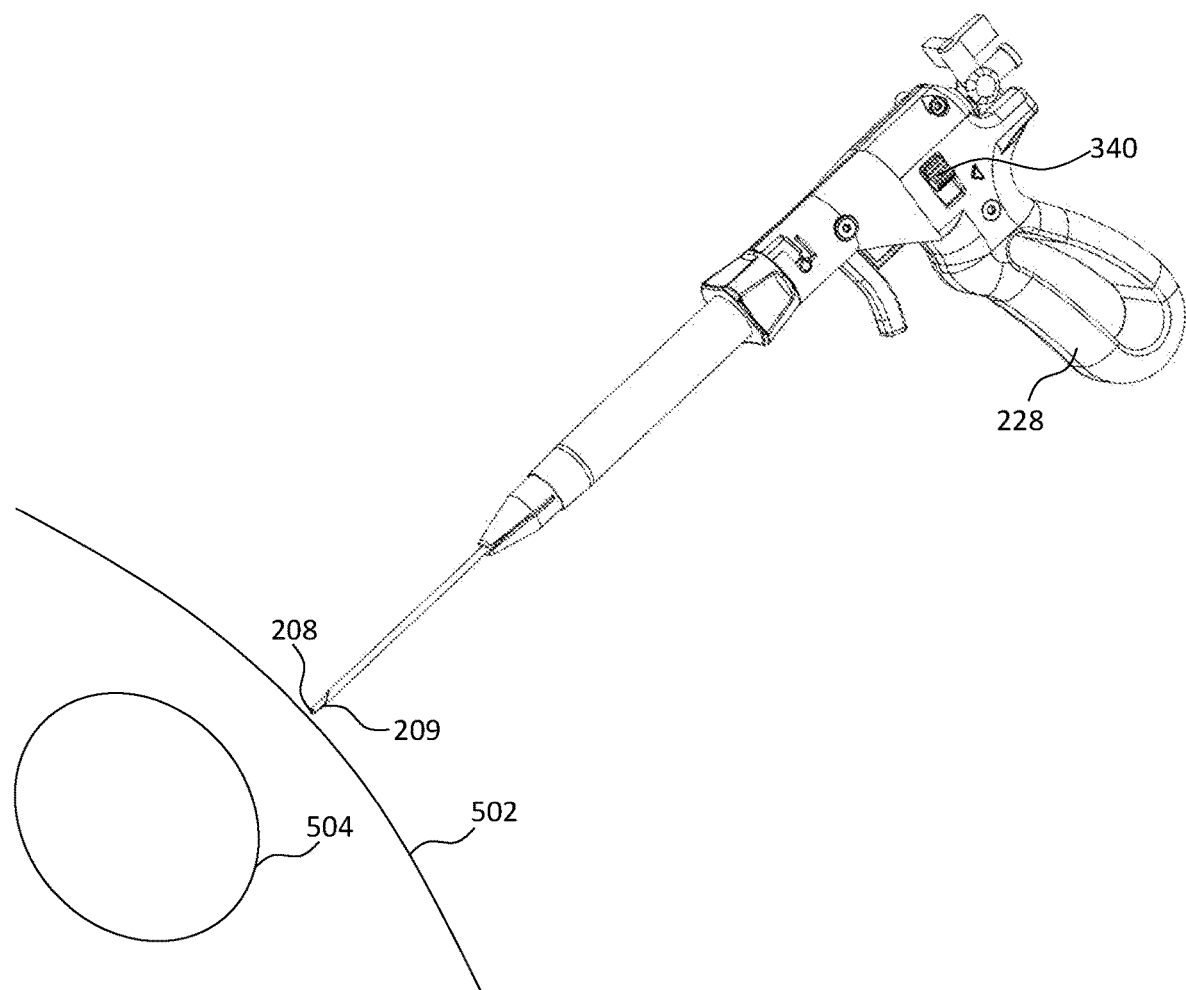
FIG. 5 illustrates a safety needle contacting skin according to aspects of the present invention.

FIG. 5 illustrates a safety needle contacting skin according to aspects of the present invention.

Prior to inserting access device 100 into a patient, a user will typically palpate the skin 502 to determine the appropriate insertion point to approach target 504. Target 504 is typically an area in the body filled with fluid that needs to be drained. Once the desired location is found, the user begins to insert access device 100.

When inserting access device 100 into the patient, safety needle 110 is the first component to contact skin 502. Pushing safety needle 110 against skin 502 causes inner cannula 208 to retract, exposing sharp tip 209 to skin 502. As the user continues to push access device 100, sharp tip 209 cuts through skin 602 and any other soft tissues including, but not limited to, muscle, fat, and fascia.

Figure 6:
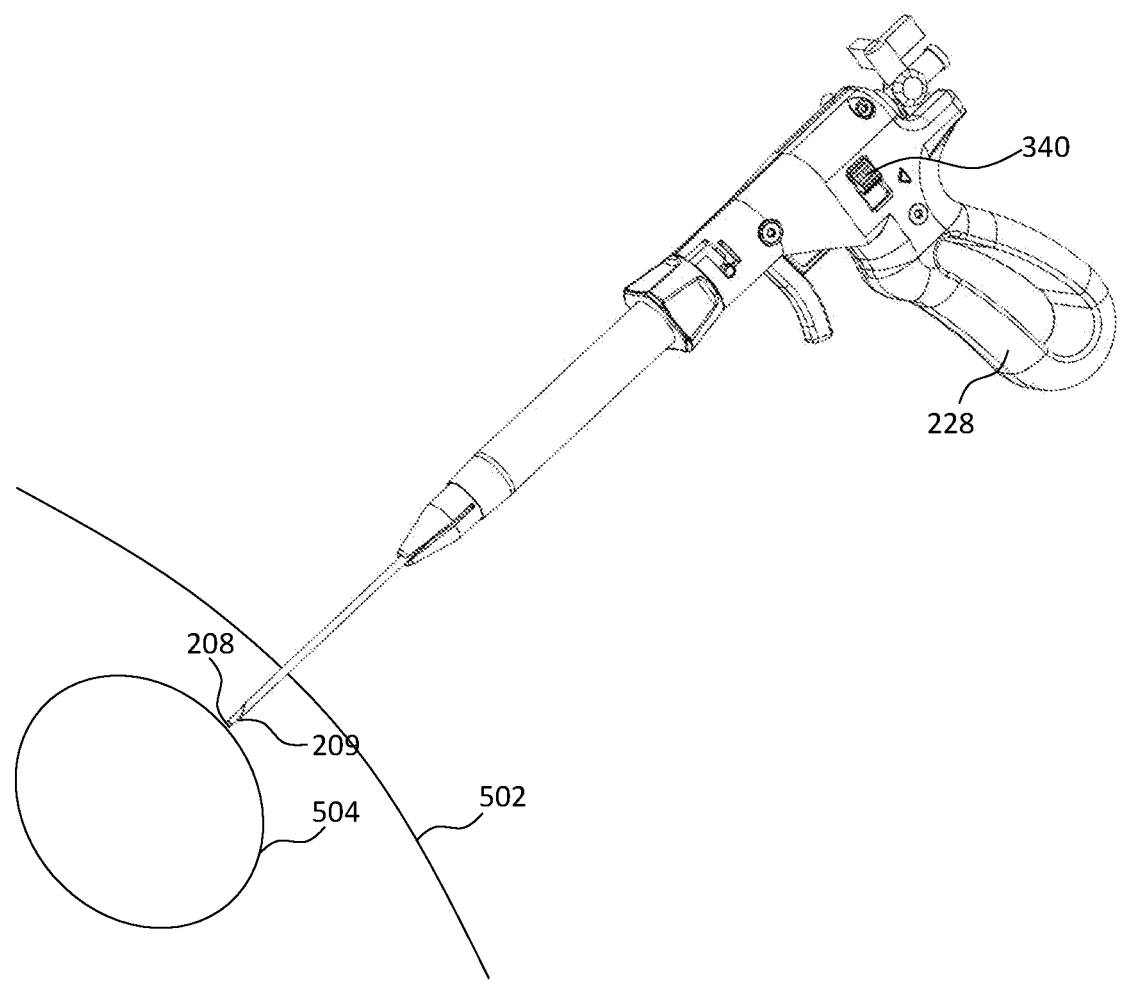
FIG. 6 illustrates a safety needle contacting a target according to aspects of the present invention.

FIG. 6 illustrates a safety needle contacting a target according to aspects of the present invention.

As the user continues to push access device 100, sharp tip 209 will eventually reach the boundary of target 504, and sharp tip 209 will puncture target 504.

Figure 7:
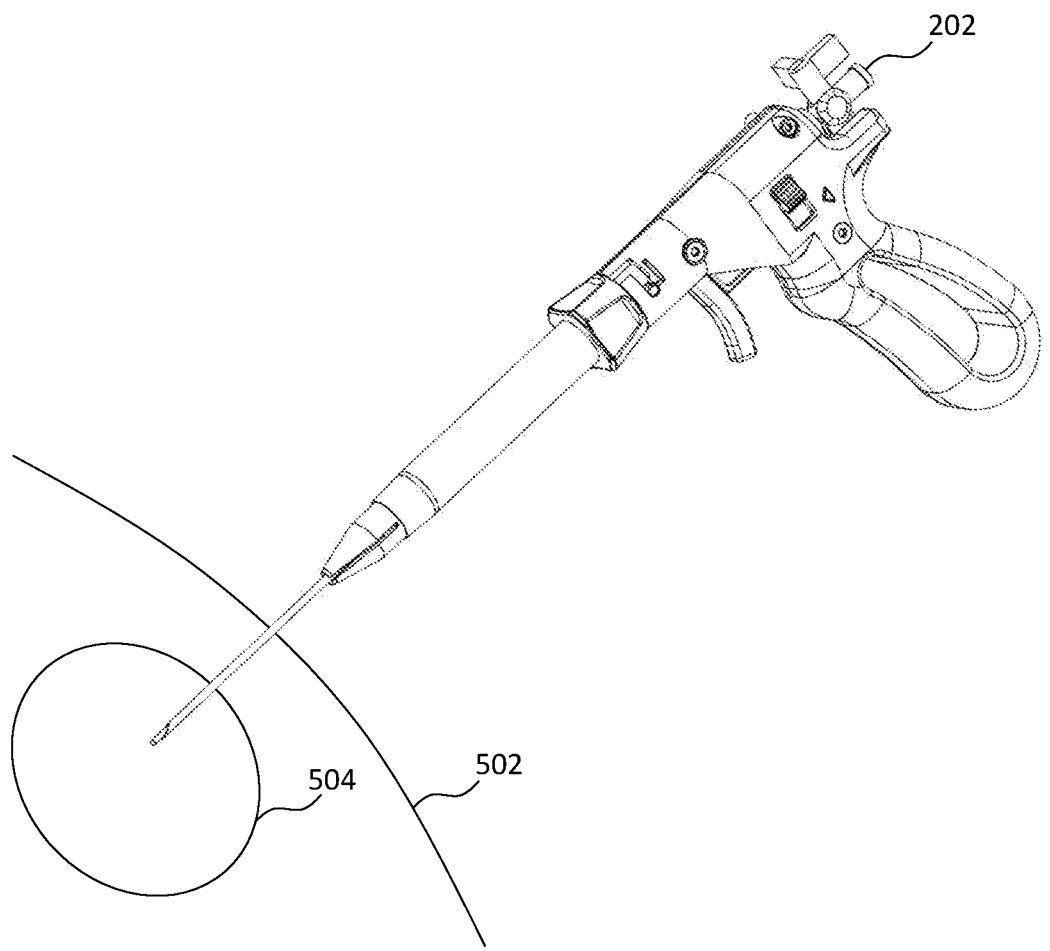
FIG. 7 illustrates aspiration of a sample according to aspects of the present invention.

FIG. 7 illustrates aspiration of a sample according to aspects of the present invention.

After sharp tip 209 punctures fluid filled target 504, the resistance from skin and tissue that exposed sharp tip 209 is eliminated and blunt tip 220 extends beyond sharp tip 209. A skilled user can sense the drop in resistance and will then seek to confirm that safety needle 110 is in the desired location. To confirm that safety needle 110 is in target 504, the user will attach a fluid drainage device to hub 202, and then the user will attempt to draw fluid from the area. If the desired fluid is drawn from the area, the user may continue with the procedure. If the desired fluid is not drawn from the area, the user may need to continue in attempts to find the desired location.

Figure 8:
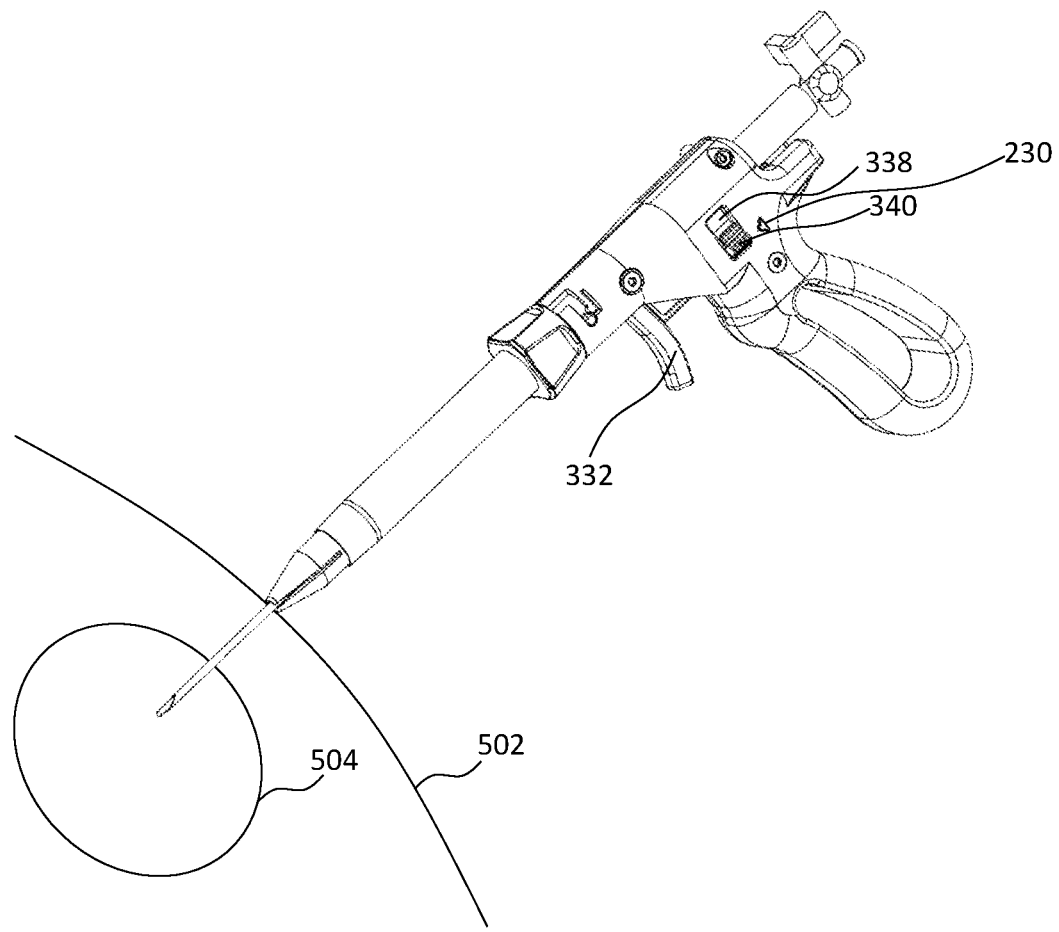
FIG. 8 illustrates releasing a lock assembly according to aspects of the present invention.

FIG. 8 illustrates releasing a lock assembly according to aspects of the present invention.

After the user confirms safety needle 110 is in the desired location, the user must release lock assembly 212 to continue with the procedure. To release lock assembly 212, the user must push button 340 and/or button 342 down. Referring back to the discussion of FIG. 3, pushing buttons 340 and/or 342 down will move lock assembly down as locking tabs 344 and 346 move past projections 308 and 316. The user may hear an audible click when lock assembly 212 has reached the unlocked position. Additionally, the user may see that button 340 will line up with indicator 230. Furthermore, the user may see visual indicator 338 through window 313. Visual indicator 230 may be a bright color to alert the user that lock assembly 212 is in the unlocked position. When lock assembly 212 is in the unlocked position, locking aperture 248 is longitudinally coaxial with actuator stem 332. Furthermore, when lock assembly 212 is in the unlocked position, safety needle lock 352 no longer prohibits longitudinal movement of safety needle 110.

Figure 9:
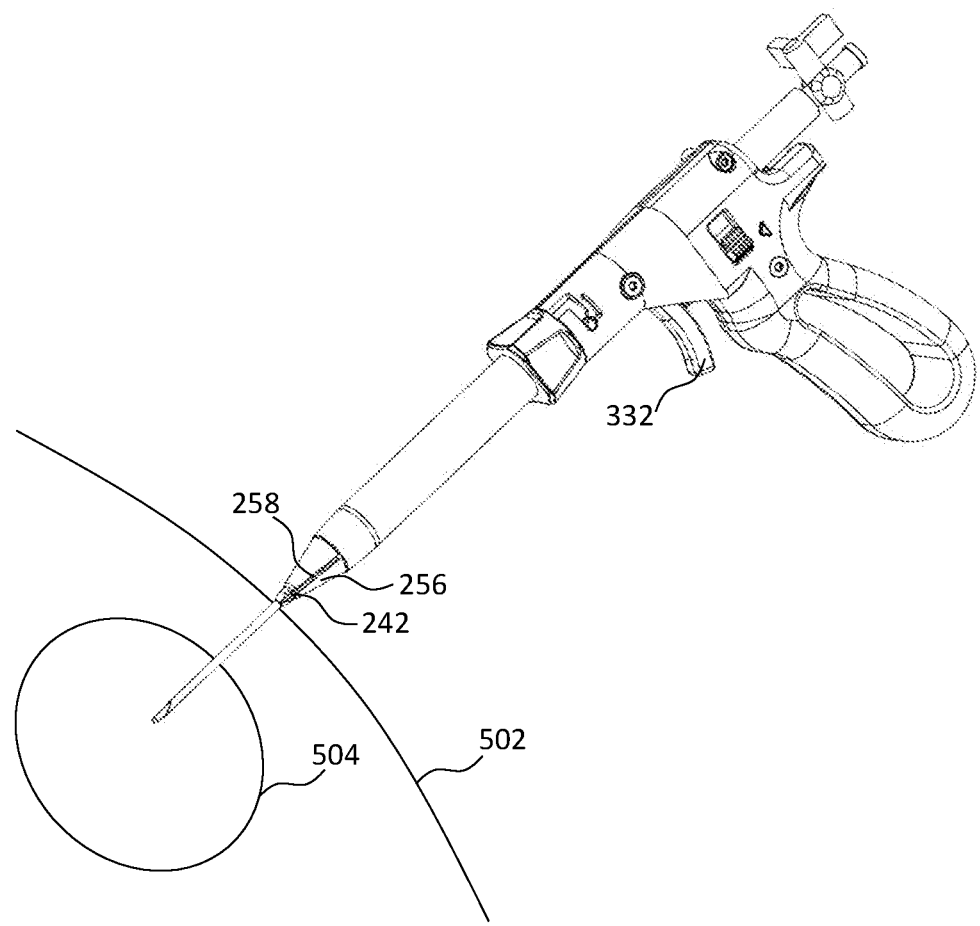
FIG. 9 illustrates exposing a blade according to aspects of the present invention.

FIG. 9 illustrates exposing a blade according to aspects of the present invention.

With lock assembly 212 in the unlocked position, the user will then pull trigger 322 proximally. Referring to FIG. 3, when the user pulls trigger 322 in the proximal direction, actuator stem 332 extends through locking aperture 248. Referring back to FIG. 4B, when the user pulls trigger 322 in the proximal direction, spring 418 is compressed as obturator assembly 106 moves proximally with trigger 322 and actuator assembly 210. Because blade assembly 108 is fixed to spring rest 402, and spring rest 402 is fixed to handle assembly 102, blade assembly 108 remains stationary as obturator assembly 106 moves in the proximal direction. As obturator assembly 106 moves in the proximal direction, distal end 256 moves in the proximal direction as well, and blades 242 are exposed through blade slot 258.

Figure 10:
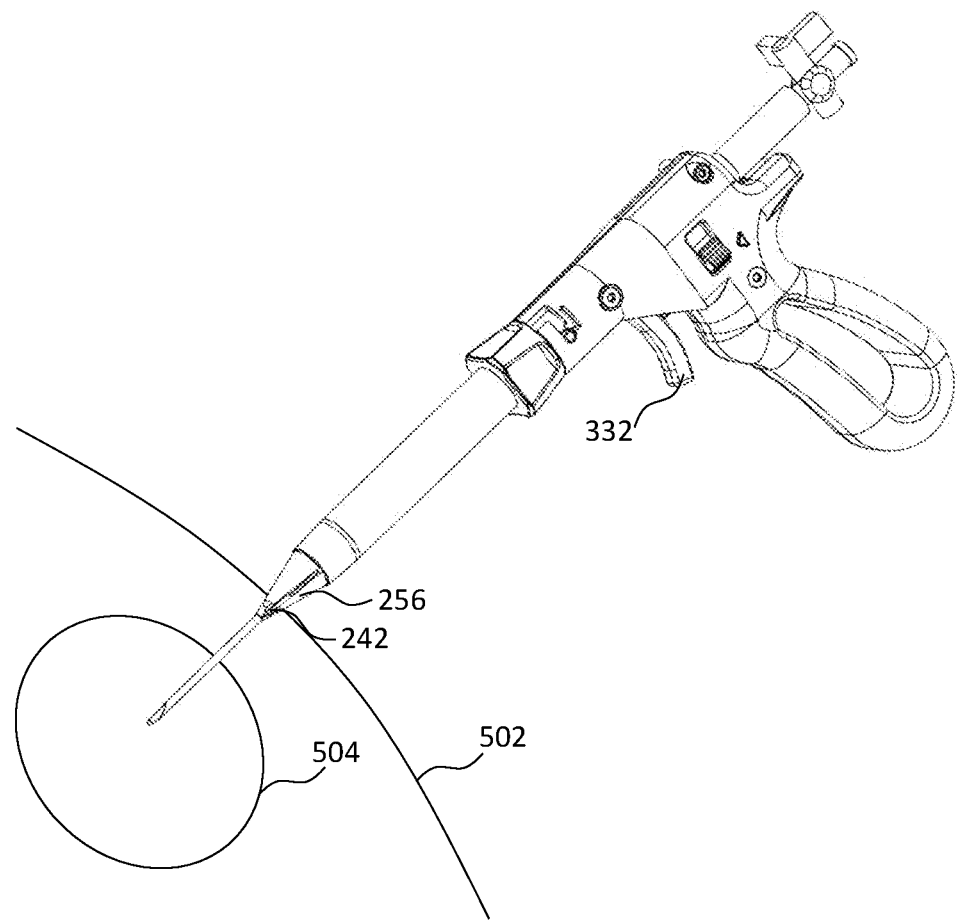
FIG. 10 illustrates advancing a blade through skin and other regions according to aspects of the present invention.

FIG. 10 illustrates advancing a blade through skin and other regions according to aspects of the present invention.

After blades 242 are exposed, the user will push access device further into skin 502 such that blades 242 expand the size of the pathway created by safety needle 110. To keep blades 242 exposed as the user advances access device 100, the user must continue to squeeze trigger 332. The user may choose to keep blades 242 exposed until reaching target 504.

Alternatively, the user may choose to release trigger 332 to cover blades 242 and move lock assembly 212 to the locked position, and then use the blunt distal end 256 to expand the pathway.

Figure 11:
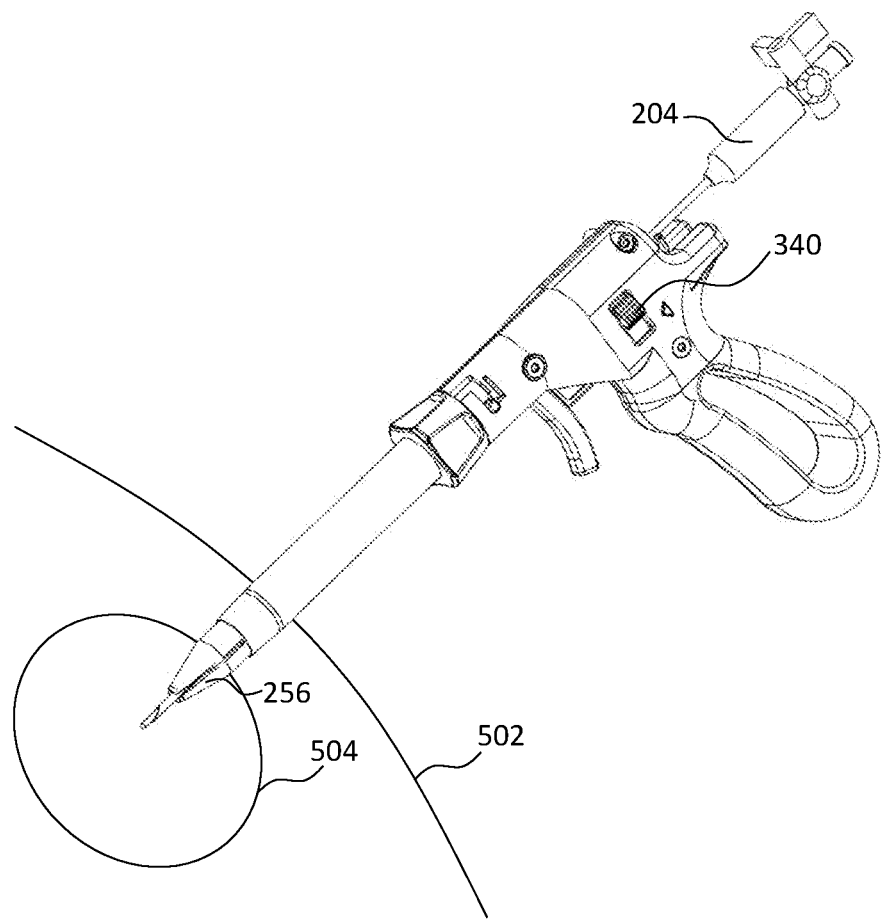
FIG. 11 illustrates removing a safety needle from an access device according to aspects of the present invention.

FIG. 11 illustrates removing a safety needle from an access device according to aspects of the present invention.

After distal end 256 reaches target 504, safety needle 110 can be removed from access device 100. To remove safety needle 110, lock assembly 212 must be in the unlocked position such that hub 204 is not constrained by safety needle lock 352. After lock assembly 212 is placed in the unlocked position, the user can remove safety needle 110 by pulling hub 204 in the proximal direction until safety needle 110 is completely removed.

Figure 12:
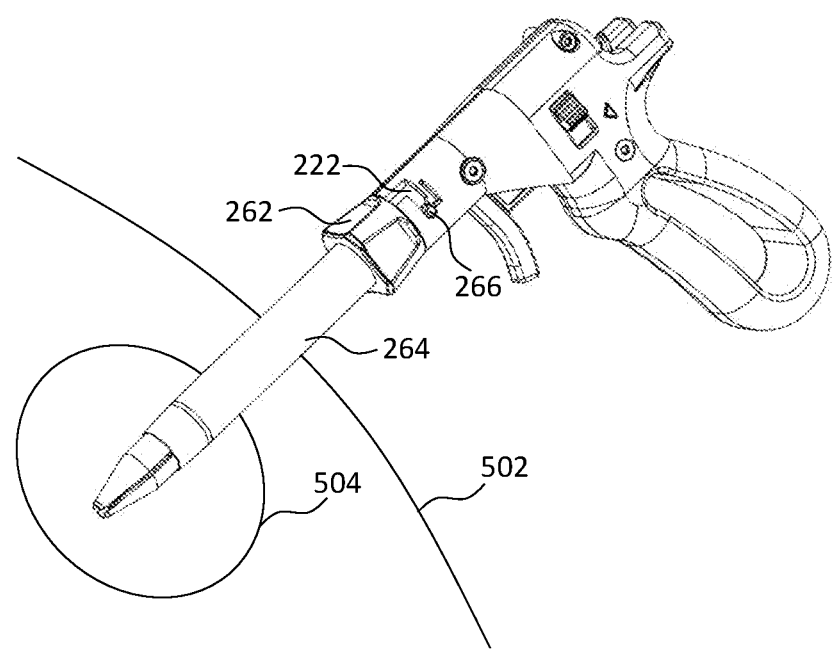
FIG. 12 illustrates an access device in the target position according to aspects of the present invention.

FIG. 12 illustrates an access device in the target position according to aspects of the present invention.

After safety needle 110 is removed, cannula shaft 264 must be positioned within target 504. If cannula shaft 264 was not positioned within target 504 when safety needle 110 was removed, the user must push access device 100 distally until cannula shaft 264 is positioned within target 504.

Figure 13:
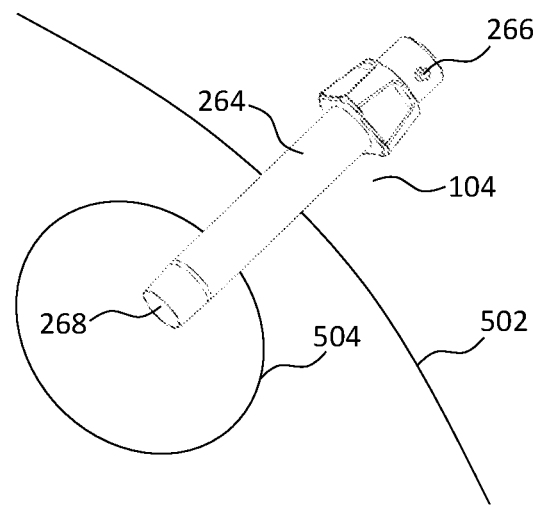
FIG. 13 illustrates a cannula remaining in the target position according to aspects of the present invention.

FIG. 13 illustrates a cannula remaining in the target position according to aspects of the present invention.

After cannula shaft 264 is properly positioned within cannula shaft 264, cannula assembly 104 can be removed from handle assembly 102. To remove cannula assembly 104 from handle assembly 102, and with reference to FIG.

2, the user will rotate cannula assembly 104 with respect to handle assembly 102 such that protrusion 266 moves within cannula slot 222 past cannula slot tab 224. Then the user will hold cannula shaft 264 stationary while pulling user grip 228 distally such that protrusion 266 exits cannula slot 222. The user will continue to pull user grip 228 distally, which will remove obturator assembly 106 and blade assembly 108 from lumen 268.

Then, cannula assembly 104 is left in the patient with lumen 268 extending from target 504 outside of skin 502, providing access to target 504. The user will typically then place a catheter through lumen 268 to reach target 504. After the catheter is in the desired location, cannula assembly 104 is then removed from the patient, and the user completes the procedure by closing the skin around the catheter.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A device to access interior body regions comprising:
   a piercing device operable to create pathway through skin and into said interior body regions;
   a blade assembly operable to cut tissue and said skin to expand said pathway, said blade assembly further comprising a blade connected to a distal end of a blade shaft, a first lumen extending longitudinally through said blade shaft, said first lumen sized and configured to slidably receive said piercing device;
   an obturator assembly operable to further expand said pathway, said obturator assembly further comprising an obturator proximal end, an obturator distal end, an obturator shaft connected to said obturator proximal end and said obturator distal end, and a second lumen extending longitudinally through said obturator proximal end, said obturator distal end, and said obturator shaft, said second lumen sized and configured to slidably receive said blade assembly;
   a cannula assembly operable to maintain said pathway and provide access to said interior body regions, said cannula assembly further comprising a cannula hub connected to a cannula shaft, and a third lumen extending longitudinally through said cannula hub and said cannula shaft, said third lumen sized and configured to slidably receive said obturator assembly;
   an actuator assembly comprising at least one actuator tab, an actuator stem, and a fourth lumen extending longitudinally through a trigger, said fourth lumen sized and configured to slidably receive said obturator assembly;
   a lock assembly comprising a safety needle lock, a locking aperture, and a button connected to a locking rail, said locking aperture sized and configured to slidably receive said actuator stem, said safety needle lock sized and configured to engage said piercing device; and
   a handle comprising a longitudinal slot, a transverse slot, and a window, said longitudinal slot sized and configured to slidably receive said actuator tab, said transverse slot sized and configured to slidably receive said locking rail, and said window sized and configured to slidably receive said button.

2. The device of claim 1, wherein said blade assembly further comprises a retaining ring attached to a proximal portion of said blade shaft, a washer proximal to and in contact with said retaining ring, a spring sized and configured to slidably receive said blade shaft and within said fourth lumen, and a spring rest.

3. The device of claim 2, wherein said spring rest further comprises a hole and a threaded hole, said hole sized and configured to slidably receive said blade shaft, said threaded hole sized and configured to receive a threaded connector.

4. The device of claim 3, wherein said obturator distal end further comprises a blade slot sized and configured to allow ingress and egress of said blade.

5. The device of claim 4, wherein said obturator proximal end further comprises a shelf, said shelf promoting assembly of said obturator proximal end to said fourth lumen in a single orientation.

6. The device of claim 5, wherein said handle further comprises a locking slot and a projection within said locking slot, said locking slot extending from said transverse slot.

7. The device of claim 6, wherein said handle further comprises a cannula slot and a cannula slot tab, said cannula slot sized and configured to allow a protrusion to move within said cannula slot, said cannula slot tab sized and configured to engage said protrusion.

8. The device of claim 7, wherein said actuator assembly further comprises a flat section sized and configured to contact said shelf when said obturator proximal end is inserted into said fourth lumen.

9. The device of claim 8, wherein said lock assembly further comprises a locking stem and a locking tab, said locking tab extending from said locking stem, said locking stem sized and configured to slide within said locking slot, and said locking tab sized and configured to engage with said projection.

* * * * *

UNITED STATES PATENT AND TRADEMARK OFFICE
CERTIFICATE OF CORRECTION

PATENT NO. : 10,779,857 B2  
APPLICATION NO. : 15/944792  
DATED : September 22, 2020  
INVENTOR(S) : Jon Kiev Page 1 of 1

It is certified that error appears in the above-identified patent and that said Letters Patent is hereby corrected as shown below:

In the Specification

At Column 4, Line 58, "connected" should be -- connected to --.

At Column 10, Line 60, "cannula assembly 108" should be -- cannula assembly 104 --.

At Column 11, Line 2, "cannula assembly 108" should be -- cannula assembly 104 --.

At Column 11, Line 21, "handle assembly 210" should be -- handle assembly 102 --.

At Column 11, Line 27, "handle assembly 210." should be -- handle assembly 102. --.

At Column 11, Line 58, "hub 202" should be -- hub 204 --.

At Column 12, Line 13, "aperture 248" should be -- aperture 348 --.

At Column 12, Line 22, "aperture 248." should be -- aperture 348. --.

At Column 12, Line 39, "trigger 332." should be -- trigger 322. --.

At Column 12, Line 41, "trigger 332" should be -- trigger 322 --.

Signed and Sealed this  
Tenth Day of August, 2021

Drew Hirshfeld  
*Performing the Functions and Duties of the  
Under Secretary of Commerce for Intellectual Property and  
Director of the United States Patent and Trademark Office*